US009839414B2

(12) United States Patent
Matsuno et al.

(10) Patent No.: US 9,839,414 B2
(45) Date of Patent: Dec. 12, 2017

(54) BIOPSY SYSTEM (71) Applicant: OLYMPUS CORPORATION, Tokyo (JP)

(72) Inventors: Kiyotaka Matsuno, Sagamihara (JP); Hirofumi Eto, Tokyo (JP); Katsuji Uemichi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 566 days.

(21) Appl. No.: 14/471,883

(22) Filed: Aug. 28, 2014

(65) Prior Publication Data
US 2015/0087994 A1    Mar. 26, 2015

Related U.S. Application Data (63) Continuation of application No. PCT/JP2013/082863, filed on Dec. 6, 2013.
(Continued)

(51) Int. Cl.
*A61B 5/05* (2006.01)
*A61B 10/04* (2006.01)
(Continued)

(52) U.S. Cl.
CPC .......... *A61B 10/04* (2013.01); *A61B 1/00133* (2013.01); *A61B 1/018* (2013.01);
(Continued)

(58) Field of Classification Search
CPC .... A61B 8/00; A61B 8/08; A61B 8/12; A61B 17/3478
See application file for complete search history.

(56) References Cited

U.S. PATENT DOCUMENTS 4,246,902 A    1/1981  Martinez
6,419,641 B1   7/2002  Mark et al.
(Continued)

FOREIGN PATENT DOCUMENTS

JP    10-118072 A     5/1998
JP    2002-051973 A   2/2002
(Continued)

OTHER PUBLICATIONS

Extended Supplementary European Search Report dated Sep. 27, 2016 in related European Patent Application No. 13 87 5004.7.
(Continued)

*Primary Examiner* — Joel Lamprecht
(74) *Attorney, Agent, or Firm* — Scully, Scott, Murphy & Presser, P.C.

(57) ABSTRACT

In the biopsy system according to one embodiment, the needle tube of the treatment tool has the minor axis of the flattened portion and the bending plane of the bending portion parallel to each other. Accordingly, the needle tube is easily bent in the bending direction of the bending portion, and even in an endoscope that has few bendable directions and is bendable, for example, in only two directions (e.g., up and down), the bending operation of the bending portion is not easily hindered. As a result, even after the treatment tool for endoscopes is inserted into the endoscope, the bending portion can be easily bent with a predetermined bending amount, and a procedure can be easily performed.

8 Claims, 9 Drawing Sheets

Related U.S. Application Data (60) Provisional application No. 61/765,196, filed on Feb. 15, 2013.

(51) Int. Cl.
| | | |
|---|---|---|
| *A61B 8/12* | (2006.01) | |
| *A61B 1/018* | (2006.01) | |
| *A61B 8/08* | (2006.01) | |
| *A61B 10/02* | (2006.01) | |
| *A61B 17/00* | (2006.01) | |
| *A61B 17/34* | (2006.01) | |
| *A61B 1/00* | (2006.01) | |
| *A61B 8/00* | (2006.01) | |
| *A61B 90/00* | (2016.01) | |

(52) U.S. Cl.
CPC .............. *A61B 8/0841* (2013.01); *A61B 8/12* (2013.01); *A61B 10/0233* (2013.01); *A61B 17/00234* (2013.01); *A61B 17/3403* (2013.01); *A61B 17/3478* (2013.01); *A61B 8/4416* (2013.01); *A61B 2010/045* (2013.01); *A61B 2017/0034* (2013.01); *A61B 2017/3413* (2013.01); *A61B 2090/3925* (2016.02)

(56) References Cited

U.S. PATENT DOCUMENTS

| | | |
|---|---|---|
| 2004/0133124 A1 | 7/2004 | Bates et al. |
| 2009/0221873 A1* | 9/2009 | McGrath ............ A61B 1/00128 600/153 |
| 2010/0228084 A1* | 9/2010 | Sato .................... A61B 8/12 600/106 |
| 2012/0220894 A1 | 8/2012 | Melsheimer |

FOREIGN PATENT DOCUMENTS

| | | |
|---|---|---|
| JP | 2002-224022 A | 8/2002 |
| JP | 3890013 B2 | 3/2007 |
| JP | 2011-510794 A | 4/2011 |
| JP | 2012-095889 A | 5/2012 |
| WO | WO 2009/100106 A1 | 8/2009 |
| WO | WO 2012/165303 A1 | 12/2012 |

OTHER PUBLICATIONS

International Search Report dated Jan. 7, 2014 issued in PCT/JP2013/082863.
English Abstract of JP 2004-181095 A, dated Jul. 2, 2004.

* cited by examiner

BIOPSY SYSTEM

CROSS-REFERENCE TO RELATED APPLICATIONS

This application is a continuation of PCT Application No. PCT/JP2013/082863 filed on Dec. 6, 2013, which claims priority to U.S. Provisional Patent Application No. 61/765,196, filed on Feb. 15, 2013, the contents of each of which are incorporated herein by reference.

TECHNICAL FIELD

The present invention relates to a biopsy system for sampling a body tissue, and more particularly, to a biopsy system including a treatment tool for endoscopes having a needle tube and an endoscope into which the treatment tool for endoscopes is inserted.

BACKGROUND ART

In the related art, an inspection method (also known as a biopsy) that samples a small amount of a body tissue and observes the tissue with a microscope is known. When a tissue of a deep part of internal organs or the like, is sampled, observation using an optical endoscope is difficult. Therefore, an ultrasonic tomogram for the internal organs by an ultrasonic endoscope or the like may be acquired, and a biopsy needle may be inserted into the internal organs under ultrasonic observation to sample a tissue. A treatment tool for the biopsy to be used for such an application is described in Japanese Unexamined Patent Application, First Publication No. 3890013 (referred to herein as "Patent Document 1"). If a distal end of the treatment tool includes a tubular needle tube that is sharply formed, and the needle tube is inserted into a tissue, a portion of the tissue enters the inside of the needle tube. By extracting the needle tube, the tissue that has entered the inside of the needle tube can be sampled.

SUMMARY OF INVENTION

Technical Problem

In a biopsy procedure using the biopsy needle described in the above Patent Document 1, an endoscope is first introduced into the vicinity of a target tissue, and the bending amount of a bending portion such that a distal end opening of a channel and an ultrasonic scanning mechanism can be located at a position where the needle tube can be suitably inserted into the target tissue is specified. Thereafter, the treatment tool equipped with the biopsy needle is inserted through the channel by releasing the bending amount first and is operated so as to be bent again by the desired bending amount. However, if the treatment tool is inserted through the channel, an insertion section is not easily bent due to the rigidity of the needle tube. As a result, even if a bending operation is performed to the maximum, there is a case where the desired bending amount is not obtained, and a procedure cannot be continued.

The invention has been made in view of such problems, and an object thereof is to provide a biopsy system in which a bending portion is easily bent even after a treatment tool for endoscopes is inserted into an endoscope.

Solution to Problem

In one embodiment, a biopsy system is provided comprising: an endoscope which includes an insertion section having a bending portion capable of being bent along a predetermined bending plane depending on an operation of an operation section; and a treatment tool for endoscopes that has a needle tube, is configured to be inserted through the endoscope, and is capable of being fixed to the endoscope by a fixing unit in a state after the treatment tool is inserted into the endoscope; wherein a portion of a distal end side of the needle tube includes a flattened portion having a major axis and a minor axis, and wherein the treatment tool for endoscopes is configured to be fixed by the fixing unit so that the minor axis of the flattened portion of the needle tube becomes parallel to the bending plane in the state after the treatment tool is inserted through the endoscope; wherein the needle tube has: a first non-flattened portion located distally relative to the flattened portion; and a second non-flattened portion located proximally relative to the flattened portion.

In one example, a length and a position of the flattened portion are configured so that the flattened portion extends over a total length of the bending portion, in both a state where the needle tube is most advanced with respect to the endoscope and a state where the needle tube is most retracted with respect to the endoscope, when the treatment tool for endoscopes is inserted through and fixed to the endoscope.

In another example, the needle tube has an opening surface at the distal end side, and the opening surface extends from a distal point of the needle tube to a point on the needle tube that is more proximal than the distal point; wherein an upper surface and a lower surface of the flattened portion are located along the minor axis; and wherein the distal point is aligned with the upper surface of the flattened portion and the point more proximal than the distal point is aligned with the lower surface of the flattened portion.

In another example, the needle tube has: a first connecting portion connecting the first non-flattened portion with the flattened portion, the first connecting portion having dimensions in a direction of the minor axis increase gradually in a taper angle in a direction moving away from the flattened portion; and a second connecting portion connecting the second non-flattened portion with the flattened portion, the second connecting portion having dimensions in a direction of the minor axis increase gradually in a taper angle in a direction moving away from the flattened portion; and wherein the taper angle of the first connecting portion is greater than the taper angle of the second connecting portion.

In another example, the treatment tool for endoscopes has a treatment tool operation unit configured to operate the needle tube, wherein the fixing unit is a holder that is provided at a distal end portion of the treatment tool operation unit and has a pair of wall portions, and wherein the operation section of the endoscope is inserted through a space between the pair of wall portions, the treatment tool operation unit is fixed to the endoscope, and thereby the operation section is fixed so that the minor axis becomes parallel to the bending plane.

In another example, the treatment tool operation unit has an operation body, a needle slider to which the needle tube is fixed and is slidably attached to the operation body, and a stopper that has a fixing screw, the stopper being attached to the operation body in order to regulate a movement range of the needle slider, and wherein an axis of the fixing screw is arranged toward an axis of the operation section of the endoscope in a state where the treatment tool for endoscopes is fixed to the endoscope.

In another example, the endoscope is an ultrasonic endoscope having an ultrasonic scanning mechanism provided on a distal end side of the bending portion.

In another example, the flattened portion has a cross-section that is essentially oval; the first non-flattened portion has a cross-section that is essentially circular; and the second non-flattened portion has a cross-section that is essentially circular.

Advantageous Effects of Invention

In the biopsy system according to one embodiment, the needle tube of the treatment tool has the minor axis of the flattened portion and the bending plane of the bending portion parallel to each other. Accordingly, the needle tube is easily bent in the bending direction of the bending portion, and even in an endoscope that has few bendable directions and is bendable, for example, in only two directions (e.g., up and down), the bending operation of the bending portion is not easily hindered. As a result, even after the treatment tool for endoscopes is inserted into the endoscope, the bending portion can be easily bent with a predetermined bending amount, and a procedure can be easily performed.

DESCRIPTION OF EMBODIMENTS

Figure 1:
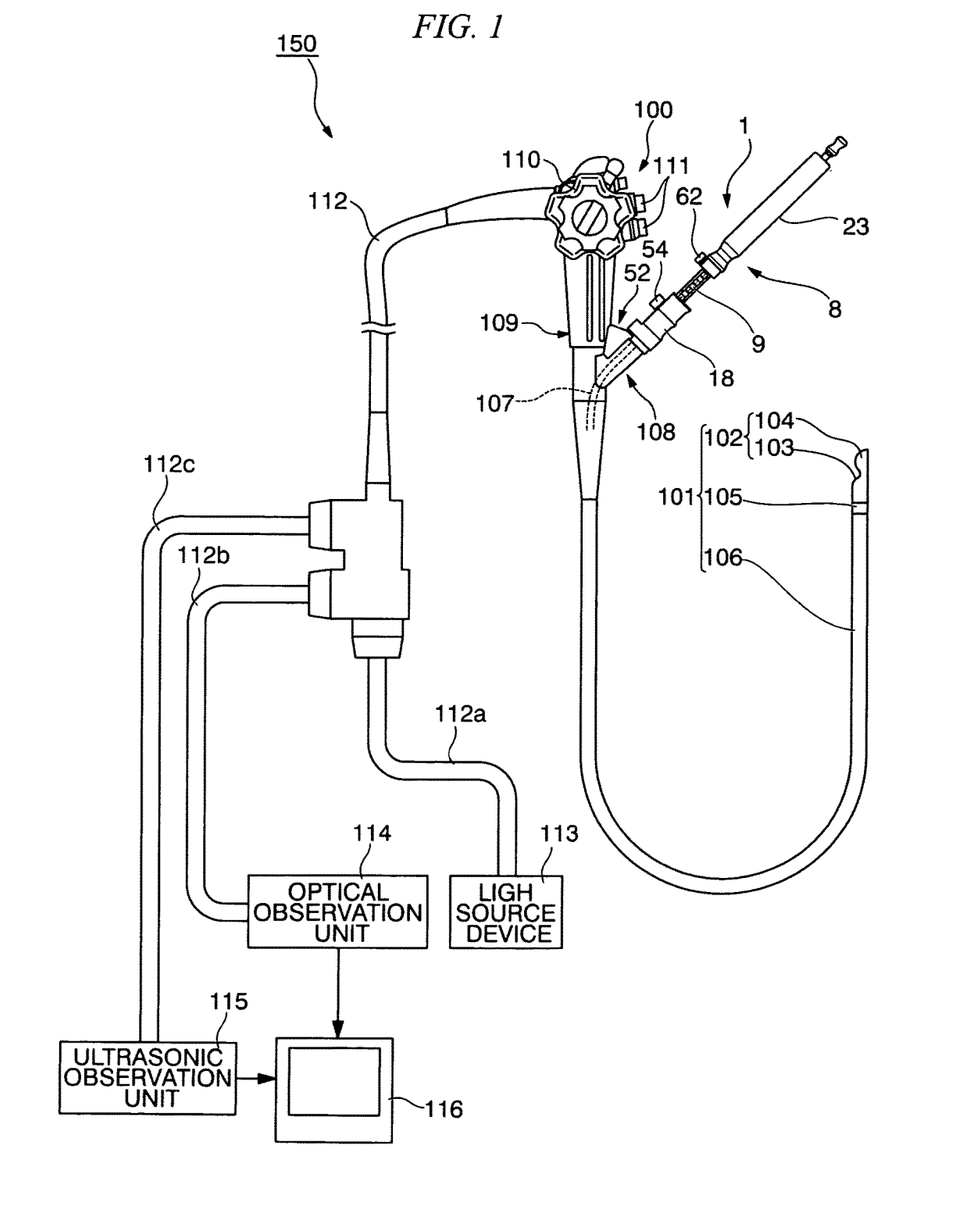
FIG. 1 is a view showing the schematic configuration of a biopsy system of a first embodiment of the invention.

An embodiment of the invention will be described with reference to FIGS. 1 to 10. First, an example of an ultrasonic endoscope to be used together with a treatment tool 1 for endoscopes (hereinafter simply referred to as a "treatment tool") in the present embodiment will be described with reference to FIG. 1. FIG. 1 is a view showing the schematic configuration of a biopsy system 150 of the present embodiment equipped with the treatment tool 1 and an ultrasonic endoscope (endoscope) 100.

As shown in FIG. 1, the ultrasonic endoscope 100 includes an insertion section 101 that is inserted into the inside of the body from a distal end, an operation section 109 that is attached to a proximal end of the insertion section 101, a universal cord 112 whose one end is connected to a side portion of the operation section 109, a light source device 113 that is connected to the other end of the universal cord 112 via a branch cable 112a, an optical observation unit 114 that is connected to the other end of the universal cord 112 via a branch cable 112b, and an ultrasonic observation unit 115 that is connected to the other end of the universal cord 112 via a branch cable 112c.

In the insertion section 101, a rigid distal end portion 102, a bending portion 105, and a flexible tube portion 106 are provided side by side in this order from a distal end side.

The rigid distal end portion 102 includes an optical imaging mechanism 103 configured to perform optical observation, and an ultrasonic scanning mechanism 104 configured to perform ultrasonic observation.

The optical imaging mechanism 103 includes various components (not shown), such as an imaging optical system in which a visual field is directed obliquely forward of the rigid distal end portion 102, an image sensor, such as a CCD or a CMOS that detects an image of a subject that has entered through the imaging optical system, and a CPU that controls the operation of the image sensor.

The ultrasonic scanning mechanism (probe) 104 includes an ultrasonic vibrator (not shown) that emits and receives an ultrasonic wave. In the ultrasonic scanning mechanism 104, a reflected wave obtained by the ultrasonic wave emitted from the ultrasonic vibrator hitting and being reflected by an object to be observed is received by the ultrasonic vibrator, and a signal based on the ultrasonic wave received by the ultrasonic vibrator is output to the ultrasonic observation unit 115.

The bending portion 105 is formed in the shape of a tube. The bending portion 105 is bent in a predetermined direction by operating so as to pull an angle wire (not shown), which is fixed to the distal end of the bending portion 105 and extends to the operation section 109, using the operation section 109. The bending portion 105 of the present embodiment can be bent in two directions along a scanning direction of the ultrasonic wave. In one example, the two directions are up and down.

In the present embodiment, for example, for the treatment of respiratory organs, there is used the endoscope in which the external diameter of the insertion section is small and which is capable of being bent in two directions. However, for example, when treatment of digestive organs is performed, there may be used an endoscope that is large in external diameter, but has a high degree of freedom in operation and is capable of being bent in four directions. In one example, the four directions are up and down and left and right.

The flexible tube portion 106 is a tubular member that is flexibly formed so as to be capable of guiding the rigid distal end portion 102 to a desired position within a lumen tissue or a body cavity.

A tubular channel 107 for allowing the treatment tool 1 to be inserted therethrough and a conduit line (not shown) configured to perform air supply, water supply, suction, or the like are provided inside each of the bending portion 105 and the flexible tube portion 106.

One end of the channel 107 opens near a distal end portion of the rigid distal end portion 102, and the other end of the channel 107 opens to a side surface of the operation section 109 on the distal end side. A proximal end mouthpiece 108 formed in the shape of a flange is fixed to the other end of the channel 107. The treatment tool 1 to be used together with the ultrasonic endoscope 100 can be fixed to the proximal end mouthpiece 108.

An external surface of the operation section 109 is formed so that a surgeon using the ultrasonic endoscope 100 can grip the operation section 109 with his/her hand. The bending operation mechanism 110 for pulling the angle wire to perform the bending operation of the bending portion 105, and a plurality of switches 111 configured to perform air supply, water supply, or suction through the conduit line are provided.

The light source device 113 is a device for emitting illumination light for taking an image with the optical imaging mechanism 103.

The optical observation unit 114 is configured so that an image taken by the image sensor of the optical imaging mechanism 103 may be projected on a monitor 116.

The ultrasonic observation unit 115 receives the signal output from the ultrasonic scanning mechanism 104, generates an image based on this signal, and projects the image on the monitor 116.

Next, the configuration of the treatment tool 1 will be described with reference to FIGS. 1 to 6.

The treatment tool 1 includes an insertion body 2 to be inserted into the inside of the body, an operation unit (treatment tool operation unit) 8 for operating the insertion body 2, and a stylet (core bar) 27.

Figure 3:
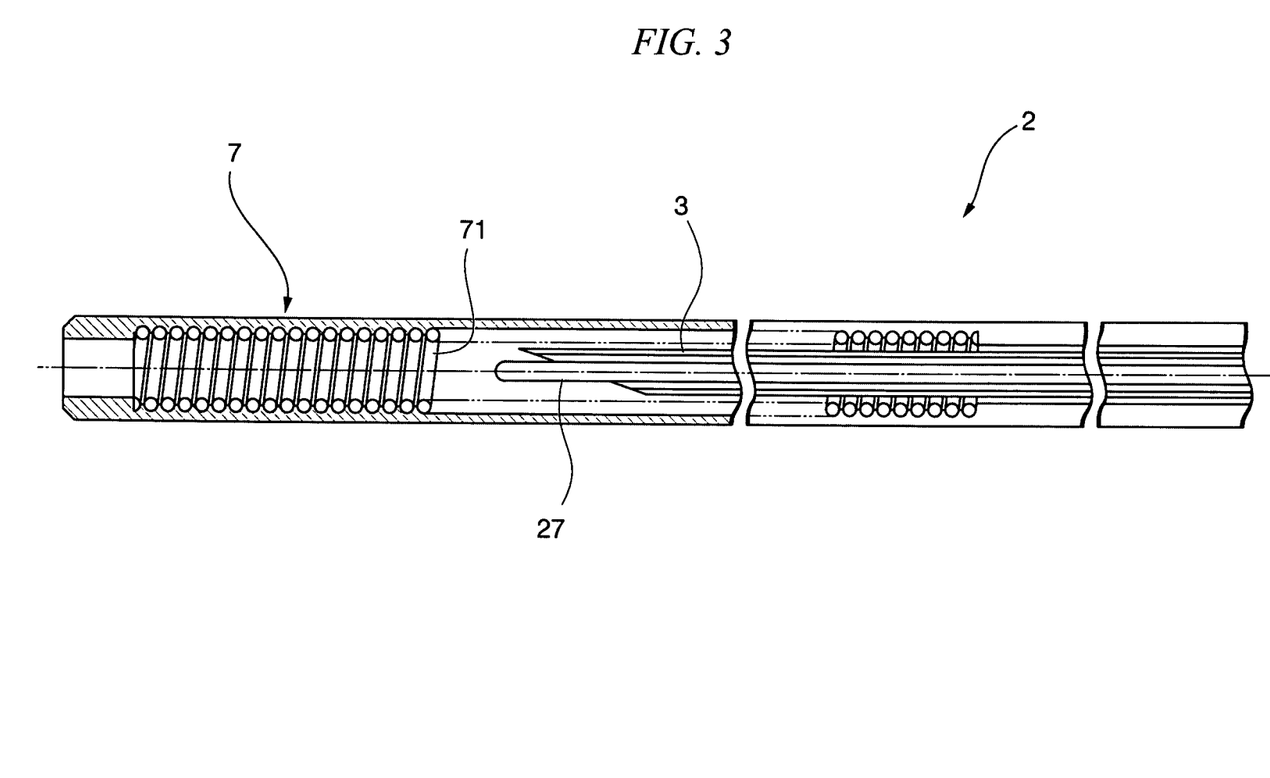
FIG. 3 is a cross-sectional view showing a distal end side of an insertion body in the treatment tool for endoscopes.

FIG. 3 is a cross-sectional view showing a distal end side of the insertion body 2. As shown in FIG. 3, the insertion body 2 includes a tubular needle tube 3 having a distal end and a proximal end, and a tubular sheath 7 through which the needle tube 3 is inserted.

As the material of the needle tube 3, a material having flexibility and having the elasticity of being easily restored to a linear state even after being bent by an external force, is preferable. For example, as the material of the needle tube 3, an alloy material, such as a stainless alloy, a nickel titanium alloy, or a cobalt chrome alloy, can be adopted.

Figure 2:
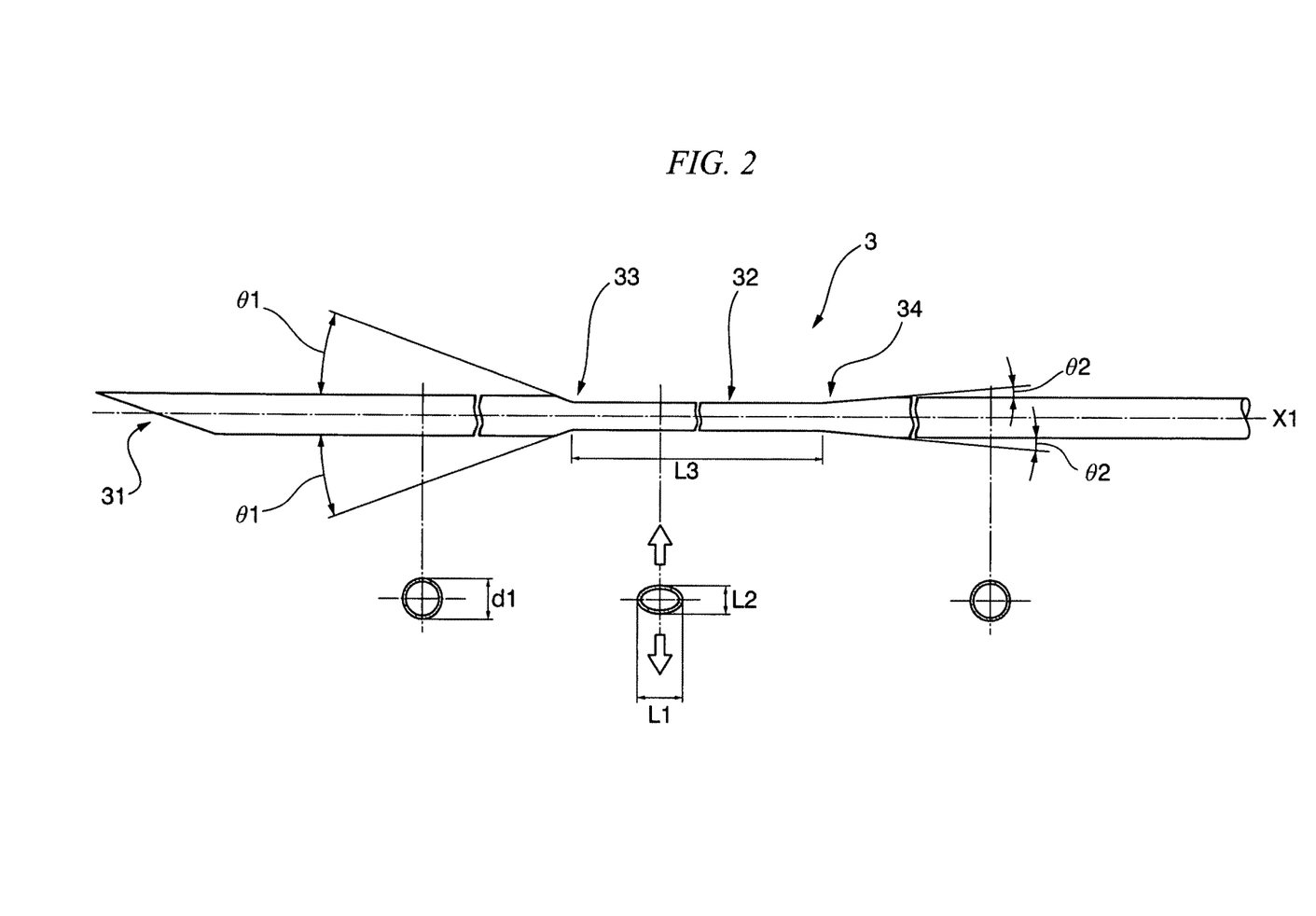
FIG. 2 is an enlarged view showing a distal end side of a needle tube of a treatment tool for endoscopes in the biopsy system.

FIG. 2 is an enlarged view of the distal end side of the needle tube 3. An opening 31 provided at a distal end of the needle tube 3 is formed by obliquely cutting off a distal end of a tubular member that forms a needle tube with respect to its own axis X1, and is sharply formed so that a living body tissue is able to be punctured. The specific shape of the opening 31 may be appropriately selected from various well-known shapes in consideration of a target tissue or the like.

The basic shape of the needle tube 3, as shown in FIG. 2, is a substantially cylindrical shape. A portion of the needle tube 3 on the distal end side is squeezed in a radial direction over a fixed length, and is formed as a flattened portion 32 having a major axis L1 and a minor axis L2 in a cross-section in a direction orthogonal to the axis X1. The length of the minor axis L2 is a value smaller than an external diameter d1 in the basic shape of the needle tube 3.

In the operation in use of the treatment tool 1 to be described below, the length L3 of the flattened portion 32 and the positions of the distal end and the proximal end are set so that the flattened portion 32 is always located over the total length of the bending portion 105 of the ultrasonic endoscope 100. That is, the flattened portion 32 is located so as to extend over the total length of the bending portion 105 in both a state where the needle tube 3 is protruded (advanced) most from the ultrasonic endoscope 100 in use and in a state where the needle tube 3 is retracted most within the channel 107.

In the flattened portion 32, it is preferable that, if a direction in which the major axis L1 extends is defined as a planar direction and a direction in which the minor axis L2 extends is defined as a thickness direction, the thickness direction of the flattened portion 32 substantially coincides with the orientation of an opening surface 31a of the opening 31. In the present embodiment, the "orientation of the opening surface" means a direction in which a normal line to the opening surface extends, at an intersection point between the opening surface and the axis X1. In addition, "the thickness direction and the orientation of the opening surface coincide with each other" means that the minor axis L2 and the normal line are located on the same plane.

A connecting portion (first connecting portion) 33 that connects the flattened portion 32 and the cylindrical region is provided on a distal end side of the flattened portion 32. A connecting portion (second connecting portion) 34 that connects the flattened portion 32 and the cylindrical region is provided on a proximal end side of the flattened portion 32. The connecting portions 33 and 34 are formed in the shape of a taper whose dimensions in the thickness direction of the flattened portion 32 increase gradually as they are separated from the flattened portion 32. A taper angle θ1 at which an outer peripheral surface of the connecting portion 33 is formed with respect to the axis X1 is, for example, is 20 degrees, and is greater than a taper angle θ2 (for example, 5 degrees) of an outer peripheral surface of the connecting portion 34. Accordingly, the dimensions of the connecting portion 33 are smaller than the dimensions of the connecting portion 34 in the direction in which the axis X1 extends.

The sheath 7 is made of, for example, a flexible tubular member, such as a metal coil or resin, and extends out of the distal end of the operation unit 8. Examples of resin that are available as the material of the sheath 7 may include polyether ether ketone (PEEK), fluorine-based resin, olefin-based resin, urethane-based resin, nylon-based (polyamide-based) resin, and the like. In the present embodiment, excessive meandering when being inserted through the channel 107 is suppressed by configuring the sheath 7 using a tube that is thinly formed from a relatively rigid high-density polyethylene (HDPE) as a material. As shown in FIG. 3, a coil 71 is arranged inside the sheath 7 to prevent the needle tube 3 from penetrating the sheath 7. The coil 71 prevents an inner cavity from being blocked when the sheath 7 is bent. In one example, the coil 71 is formed by being wound so that metal wires are not brought into contact with each other. This results in the flexibility of the sheath 7 not being greatly reduced. In one specific example, the gap between the wires becomes 0.1 mm or less.

Figure 4:
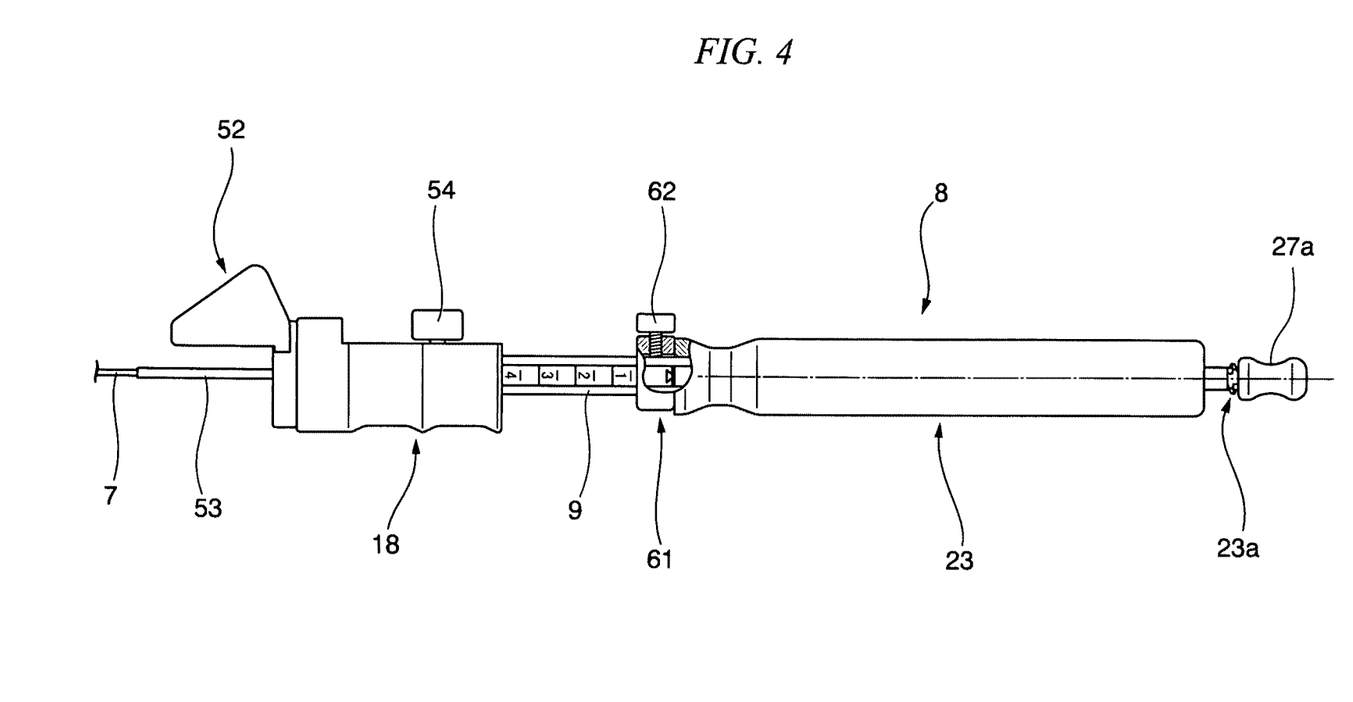
FIG. 4 is an enlarged view of an operation section of the treatment tool for endoscopes.
Figure 5:
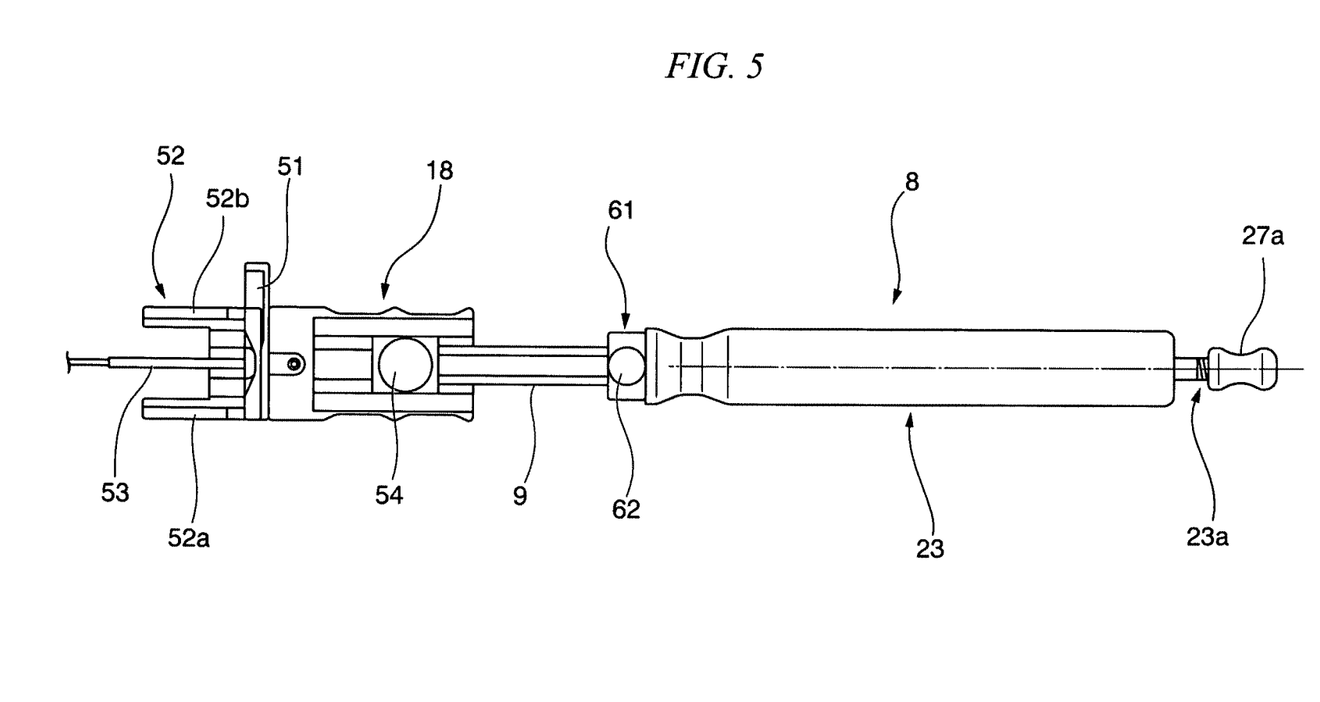
FIG. 5 is a view as seen from arrow A of FIG. 4.
Figure 6:
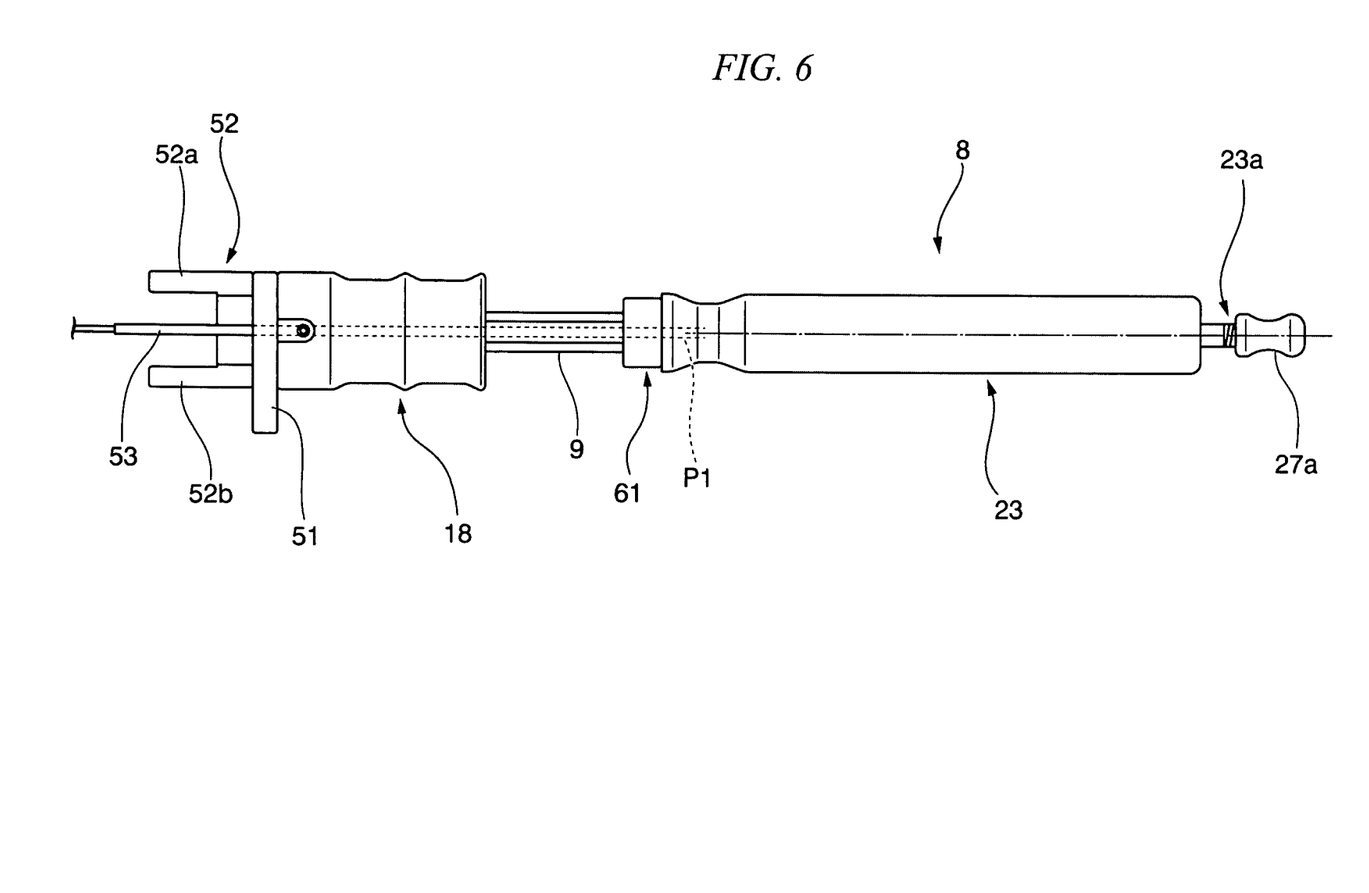
FIG. 6 is a view as seen from arrow B of FIG. 4.

FIG. 4 is an enlarged view of the operation unit 8, FIG. 5 is a view as seen from arrow A of FIG. 4, and FIG. 6 is a view as seen from arrow B of FIG. 4. The operation unit 8, as shown in FIGS. 4 to 6, includes an operation body 9, a sheath adjuster 18 that is provided on a distal end side of the operation body 9, and a needle slider 23 that is provided on a proximal end side of the operation body 9.

The operation body 9 is formed from, for example, ABS resin or the like, and has a tube cavity that allows the needle tube 3 and the sheath 7 to be inserted therethrough. The distal end side of the operation body 9 is inserted into the sheath adjuster 18 that is formed in a tubular shape. The proximal end side of the operation body 9 is inserted into the needle slider 23 that is formed in a tubular shape. The operation body 9 and the sheath adjuster 18, and the operation body 9 and the needle slider 23 are slidable in an axis direction while the relative rotation thereof around the axis is suppressed, by grooves, protrusions, or the like formed in surfaces thereof (not shown) being engaged with each other.

A distal end portion of the sheath adjuster 18 is provided with a slide lock 51 that is attachable to and detachable from the proximal end mouthpiece 108 of the ultrasonic endoscope 100. By causing the slide lock 51 to slide in a direction orthogonal to the axis of the operation unit 8 and be engaged with the proximal end mouthpiece 108, the operation unit 8 can be fixed to the ultrasonic endoscope 100. A holder (fixing unit) 52 having a pair of wall portions 52a and 52b is provided on a distal end side of the slide lock 51. The holder 52 is fixed to the sheath adjuster 18. The pair of wall portions 52a and 52b of the holder 52 are substantially parallel to each other. The distance of the wall portion 52a from the wall portion 52b is set to a value such that the distal end side of the operation section 109 of the ultrasonic endoscope 100 is firmly attached.

A supporting pipe 53 made of, for example, stainless steel, protrudes from the distal end portion of the sheath adjuster 18. A distal end portion of the supporting pipe 53 is inserted into the channel 107 when the treatment tool 1 is attached to the ultrasonic endoscope 100. The supporting pipe 53 is inserted into the operation body 9. A proximal end of the supporting pipe 53 is located further toward a proximal end side (for example, a position P1 shown in FIG. 6) than a distal end of a needle slider 23 in a state where the needle slider 23 has advanced most with respect to the operation body 9. The sheath 7 is inserted through the supporting pipe 53, and a proximal end portion thereof protrudes from the proximal end of the supporting pipe 53 and is fixed to the operation body 9 by adhesion or the like.

A fixing screw 54 is attached to the sheath adjuster 18. The fixing screw 54 is fitted to a screw hole (not shown) that is provided in the operation body 9 through the sheath adjuster 18. If the fixing screw 54 is tightened to the operation body 9, the sheath adjuster 18 is pressed against the operation body 9 so that the sheath adjuster 18 and the operation body 9 can be fixed in a non-slidable manner. By changing the positional relationship between the sheath adjuster 18 and the operation body 9, the protrusion length of the sheath 7 from the channel 107 when the operation unit 8 is fixed to the ultrasonic endoscope 100 can be adjusted, and the protrusion length can be fixed by the fixing screw 54.

Since a proximal end side of the needle tube 3 protrudes from a proximal end of the sheath 7 and is fixed to the needle slider 23, the needle tube 3 can be protruded and retracted from the distal end of the sheath 7 by causing the needle slider 23 to slide with respect to the operation body 9. On a distal end side of the needle slider 23, a stopper 61 is attached so as to be movable with respect to the operation body 9. The stopper 61 has a fixing screw 62 and can be fixed to the operation body 9 by tightening the fixing screw 62. Since the needle slider 23 can be advanced only to a position where the needle slider comes into contact with the stopper 61, the maximum protrusion length of the needle tube 3 from the sheath 7 can be adjusted by adjusting the fixed position of the stopper 61 with respect to the operation body 9.

An opening 23a is provided in a proximal end portion of the needle slider 23 so that the stylet 27 can be inserted into the needle tube 3 from the proximal end of the needle tube 3. A thread is provided in the opening 23a so that a knob 27a attached to a proximal end portion of the stylet 27 is fittable to the thread of the opening 23a. Additionally, a well-known syringe or the like is connectable to the opening 23a so that an object within the needle tube 3 can be suctioned. The stylet 27 has a cross-sectional shape that is substantially circular, has a smaller diameter than the dimensions of the minor axis L2 in the needle tube 3, and is capable of being advanced and retracted within the needle tube 3.

As shown in FIG. 1, it is preferable that the fixing screw 54 and the fixing screw 62 be arranged so that their respective axes face the axis of the operation section 109 settled in the holder 52. Accordingly, since the fixing screw 54 and the fixing screw 62 are not biased left and right when the operation unit 8 is located on the front, the operation unit can be operated easily without depending on the handedness of a surgeon. If the axes of the fixing screw 54 and the fixing screw 62 face the axis of the operation section 109 settled in the holder 52, even if the fixing screw 54 and the fixing screw 62 are attached toward a side opposite to FIG. 1, almost the same effects can be obtained.

Irregularities are provided on an outer peripheral surface of the sheath adjuster 18 and an outer peripheral surface of a distal end portion of the needle slider 23 so that a surgeon can easily grip the sheath adjuster.

The operation in use of a biopsy system 150 having the above configuration will be described. In the following, the biopsy treatment of inserting the needle tube 3 of the treatment tool 1 into a lesion located in a deep part of the lungs as a target tissue and collecting cells or the like of the lesion through the inside of the needle tube 3 will be described as an example.

First, a surgeon inserts the insertion section 101 of the ultrasonic endoscope 100 into the inside of the body, and introduces the distal end portion of the insertion section 101 to an area near a target tissue while performing observation with the optical imaging mechanism 103 and appropriately bending the bending portion 105. After the introduction, the surgeon determines a part where the biopsy is to be performed, on the basis of the observation results obtained by the optical imaging mechanism 103 and the ultrasonic scanning mechanism 104.

Figure 7:
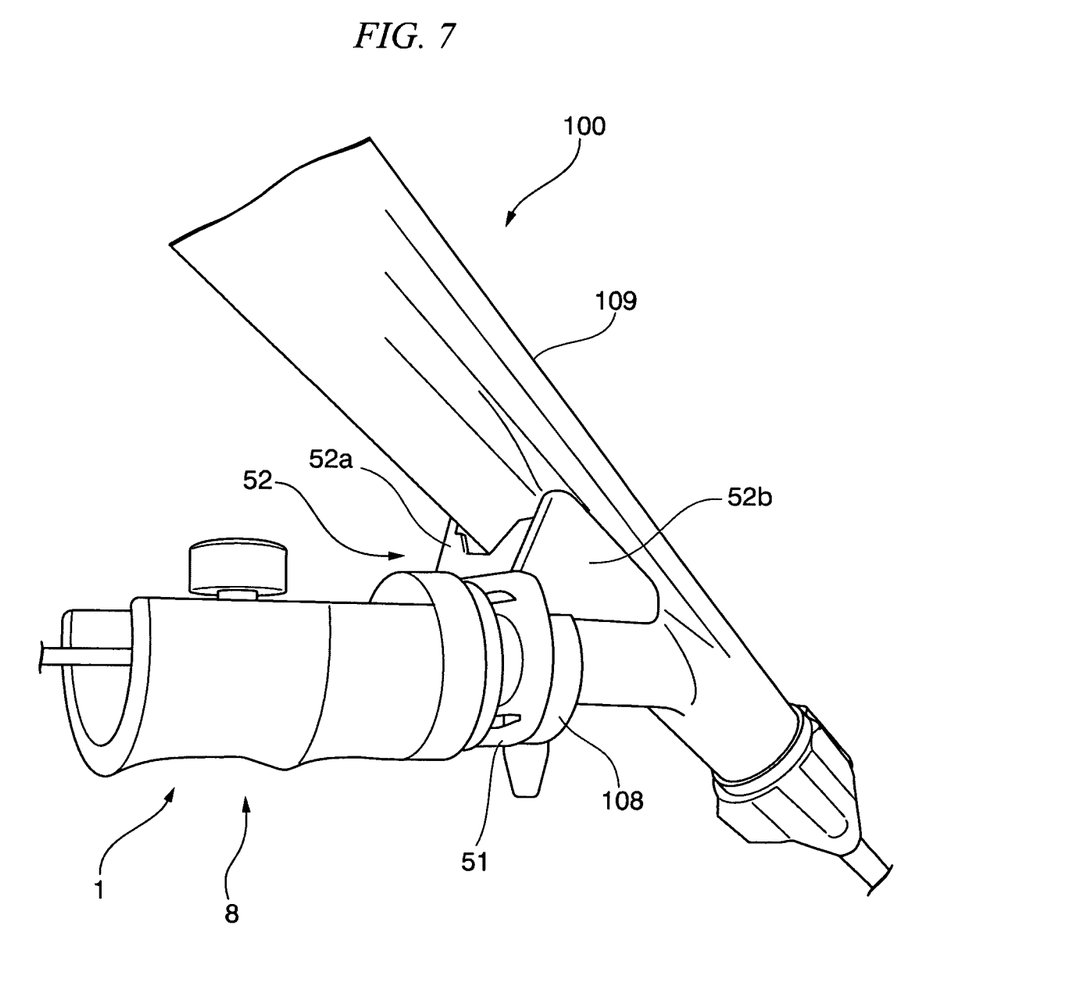
FIG. 7 is a view showing a state where the treatment tool for endoscopes is fixed to an ultrasonic endoscope.

Next, the surgeon inserts the insertion body 2 of the treatment tool 1 from the distal end side of the insertion body 2 into the proximal end mouthpiece 108 provided at the operation section 109 of the ultrasonic endoscope 100 to the inside of the channel 107. Moreover, as shown in FIG. 7, the surgeon advances the distal end side of the operation section 109 between the pair of wall portions 52a and 52b of the holder 52, and then engages the slide lock 51 provided in the operation unit 8 of the treatment tool 1 with the proximal end mouthpiece 108. Accordingly, the operation unit 8 of the treatment tool 1 is fixed to the ultrasonic endoscope 100 so as not to rotate with respect to the operation section 109.

Figure 8:
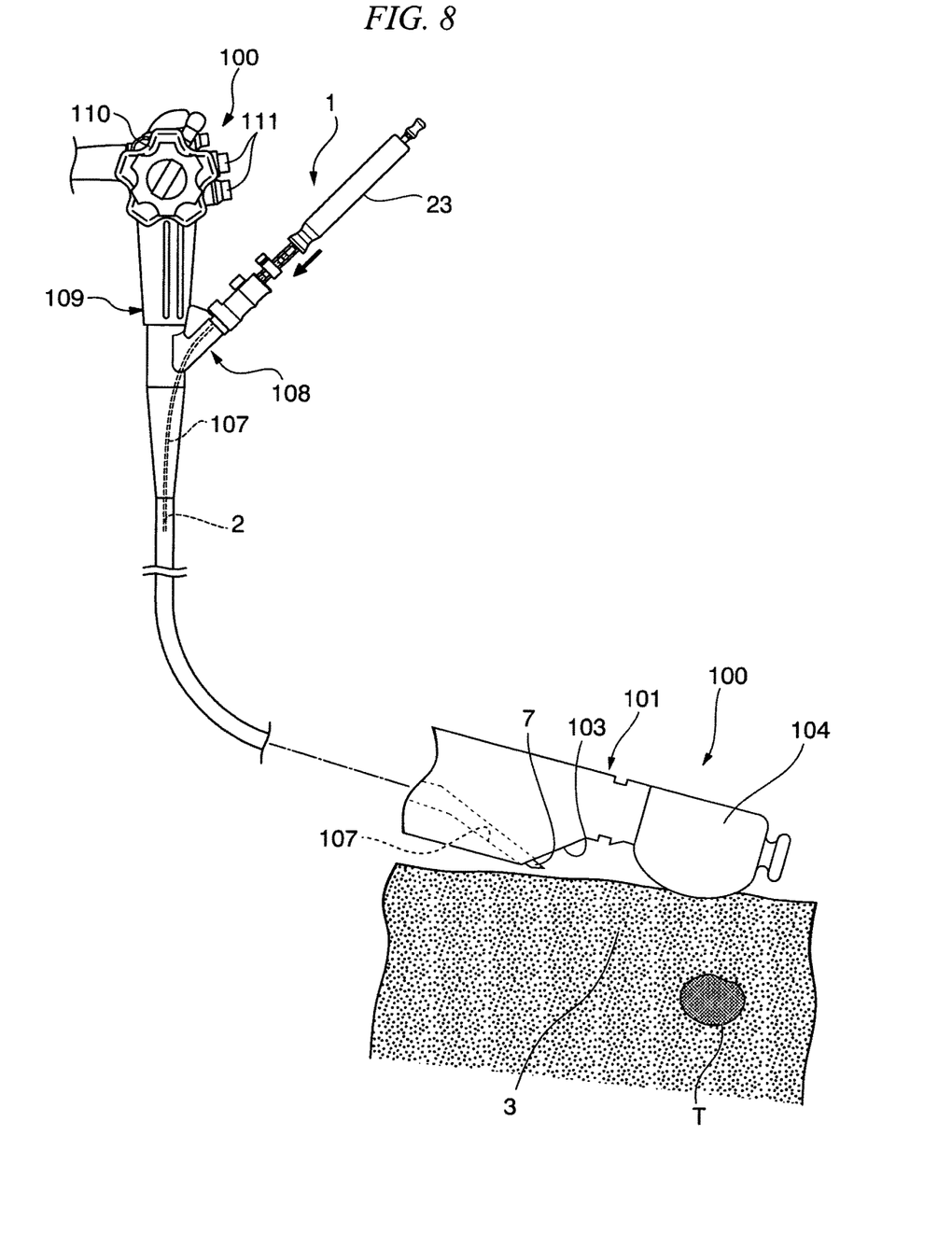
FIG. 8 is a view showing one process when the biopsy system is used.

Next, the surgeon loosens the fixing screw 54 and causes the sheath adjuster 18 and the operation body 9 to slide relative to each other as shown in FIG. 8 while observing the sheath 7 and the inside of the body using the optical imaging mechanism 103 and the ultrasonic scanning mechanism 104, thereby adjusting the protrusion amount of the sheath 7 from the distal end of the insertion section 101 of the ultrasonic endoscope 100 to a suitable amount. After the adjustment, the surgeon tightens the fixing screw 54 to fix the protrusion amount.

Next, on the basis of the observation result obtained by the ultrasonic scanning mechanism 104, the stopper 61 is moved and fixed to the operation body 9 at a desired position while taking into consideration the distance to a target tissue T where the biopsy is to be performed, and the maximum protrusion length of the needle tube 3 is adjusted.

Figure 9:
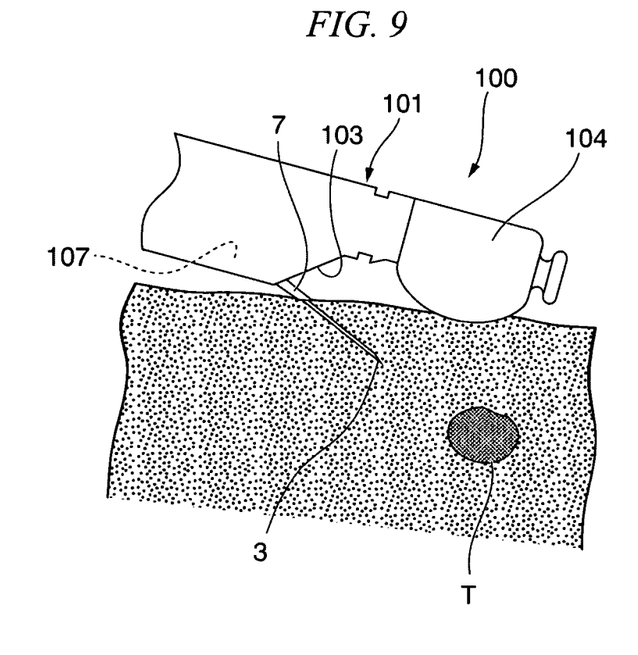
FIG. 9 is a view showing one process when the biopsy system is used.
Figure 10:
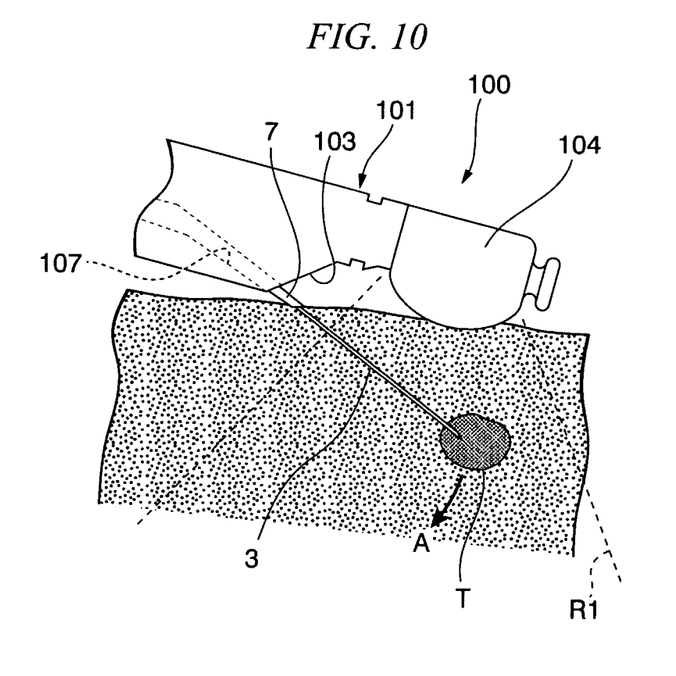
FIG. 10 is a view showing one process when the biopsy system is used.

Next, as shown in FIG. 8, the surgeon advances the needle slider 23 to the distal end side of the operation unit 8. Accordingly, as shown in FIG. 9, the needle tube 3 protrudes from the sheath 7. Moreover, as shown in FIG. 10, the distal end of the needle tube 3 punctures the tissue, and is pushed to the target tissue T where the biopsy is to be performed. At this time, the needle tube 3 exposed to the outside of the surface of the tissue can be observed by the optical imaging mechanism 103, and a distal end side portion of the needle tube 3 inserted into the inside of the tissue can be observed by the ultrasonic scanning mechanism 104.

In a state where the treatment tool 1 is fixed to the ultrasonic endoscope 100 as described above, the needle tube 3 is made to protrude from the channel 107 so that the opening surface of the distal end thereof faces the ultrasonic scanning mechanism 104 side. That is, the minor axis L2 of the flattened portion 32 of the needle tube 3 is in a positional relationship in which the minor axis is substantially orthogonal to a receiving surface of the ultrasonic scanning mechanism 104 (substantially orthogonal to at least a portion when the receiving surface has a curved surface shape). A bending plane (a virtual plane including the track of the insertion section 101 when the bending portion 105 is bent in two directions) of the bending portion 105 and the thickness direction (the direction of the minor axis L2) of the flattened portion 32 are substantially parallel to each other.

The surgeon can observe an ultrasonic image based on the ultrasonic wave received in the ultrasonic scanning mechanism 104, using the ultrasonic observation unit 115 shown in FIG. 1. The surgeon causes the distal end of the needle tube 3 to reach the target tissue T where the biopsy is to be performed, with reference to the image of the needle tube 3 that is clearly projected on the ultrasonic observation unit 115.

When the needle tube 3 is caused to protrude, the area on which a reaction force from the tissue acts perpendicularly is larger on an opening surface side than a side opposite to the opening surface side. For this reason, as shown by arrow A in FIG. 10, the distal end portion of the needle tube 3 is easily advanced obliquely forward while increasing an angle formed in conjunction with the distal end portion and the axis of the insertion section 101. As a result, the distal end portion does not easily deviate out of a scanning range R1 of the ultrasonic scanning mechanism 104. Additionally, since the opening surface faces the ultrasonic scanning mechanism 104 side, a force that moves the distal end portion of the needle tube 3 to the outside of a scanning area (almost the same as the above-described bending plane) of the ultrasonic scanning mechanism 104 is not easily generated. Accordingly, it is possible to suitably continue observing the distal end portion of the needle tube 3 with an ultrasonic image.

Next, the surgeon pushes out a tissue, which has entered the needle tube 3 and is not a biopsy target, using the stylet 27, and pulls the stylet 27 out of the insertion body 2 and the operation unit 8. Accordingly, a through-hole extending from the distal end of the needle tube 3 to a proximal end of the needle slider 23 is formed. The surgeon connects the syringe or the like to the proximal end of the needle slider 23, suctions the inside of the needle tube 3, and suctions and samples cells or the like of the target tissue T where the biopsy is to be performed from the distal end of the needle tube 3.

If a required amount of cells or the like has been sampled, the needle slider 23 is retracted to the proximal end side of the operation unit 8, and the distal end of the needle tube 3 is housed within the sheath 7. Accordingly, the needle tube 3 comes out of the tissue. If the needle tube 3 comes out of the tissue, the slide lock 51 is removed from the proximal end mouthpiece 108 of the operation section 109 of the ultrasonic endoscope 100, and the treatment tool 1 is extracted from the channel 107. Finally, the ultrasonic endoscope 100 is extracted from a patient, and a series of treatment is ended.

In the biopsy system 150 of the present embodiment, the needle tube 3 of the treatment tool 1 has the thickness direction (the direction of the minor axis L2) of the flattened portion 32 and the bending plane of the bending portion 105 parallel to each other. Accordingly, the needle tube 3 is easily bent in a bending direction of the bending portion 105, and even in an endoscope that has few bendable directions and is bendable in only two directions, the bending operation of the bending portion 105 is not easily hindered. As a result, even after the treatment tool is inserted, the bending portion can be easily bent with a predetermined bending amount, and a procedure can be easily performed.

Additionally, in the connecting portions 33 and 34 that connect the flattened portion 32 and the cylindrical regions, the taper angle θ1 of the connecting portion 33 on the distal end side is set to be greater than the taper angle θ2 of the connecting portion 34. Therefore, the dimensions of the connecting portion 33 in the axis direction can be shortened. As a result, the needle tube 3 does not easily meander within the channel 107.

Moreover, the length L3 of the flattened portion 32 is set over the total length of the bending portion 105 both when the needle tube 3 is most advanced with respect to the ultrasonic endoscope 100 and when the needle tube 3 is most retracted with respect to the ultrasonic endoscope. Therefore, during a procedure, the bending portion is easily bent, and a bent state can be stabilized.

Moreover, in the operation unit 8, the supporting pipe 53 extends until the supporting pipe reaches the needle slider 23. Therefore, the operation unit 8 can be reliably supported with respect to the ultrasonic endoscope 100, can prevent the rattling of the respective parts of the operation unit 8 during operation, and can be stably operated.

Although one embodiment of the invention has been described above, the specific configuration of the invention is not limited to this embodiment. Additions, omissions, and substitutions of components, the combinations of the contents of the embodiment, and other modifications can be made without departing from the spirit of the invention.

For example, the cross-sectional shape of the flattened portion 32 is not limited (as long as the cross-sectional shape has a major axis and a minor axis). The cross-sectional shape can be appropriately selected from various well-known shapes, for example, an elliptical shape, an oval shape, or an oblong shape whose corners are rounded off.

In the above-described embodiment, an example using the stylet in which the cross-sectional shape is a substantially circular shape with a diameter matched with the dimensions of the minor axis L2 of the flattened portion 32 has been described. However, the stylet is not limited to this, and various stylets can be used. For example, a stylet having a flattened cross-section matched with the cross-sectional shape of the flattened portion may be used. Additionally, the stylet may be formed in a hollow shape in order to reduce the advance or retraction resistance within the needle tube of the stylet. At this time, when an edge remains at a distal end of the tubular stylet, hooking may be caused within the needle tube. Therefore, such hooking may be suppressed by performing heating and melting to round off the distal end or attaching a distal end member whose distal end is rounded off to the distal end of the stylet through welding or the like.

Moreover, in order to suppress the hooking of the stylet, such machining that an inner surface of the needle tube becomes smooth may be performed.

REFERENCE SIGNS LIST

1: TREATMENT TOOL FOR ENDOSCOPE
3: NEEDLE TUBE
8: OPERATION UNIT (TREATMENT TOOL OPERATION UNIT)
31a: OPENING SURFACE
32: FLATTENED PORTION

33: CONNECTING PORTION (FIRST CONNECTING PORTION)
34: CONNECTING PORTION (SECOND CONNECTING PORTION)
52: HOLDER (FIXING UNIT)
52a, 52b: WALL PORTION
100: ULTRASONIC ENDOSCOPE
101: INSERTION SECTION
105: BENDING PORTION
109: OPERATION SECTION
150: BIOPSY SYSTEM

The invention claimed is:

1. A biopsy system comprising:
an endoscope which includes an insertion section having a bending portion capable of being bent along a bending plane depending on an operation of an operation section; and
a treatment tool having a needle tube extended in a longitudinal direction, the treatment tube being configured to be inserted through the endoscope, the treatment tube being configured to be fixed to the endoscope by a fixing unit in a state where the treatment tool is inserted into the endoscope;
wherein the needle tube has a distal end portion, a proximal end portion and a flattened portion, the distal end portion, the proximal end portion and the flattened portion each having a cross-section perpendicular to the longitudinal axis with a major axis and a minor axis;
the flattened portion being provided between the distal end portion and the proximal end portion;
the minor axis of the flattened portion having a dimension smaller than a dimension of the major axis of each of the distal end portion, the proximal end portion and the flattened portion, and
the treatment tool is configured to be fixed to the endoscope by the fixing unit such that at least one surface at the minor axis of the flattened portion is parallel to the bending plane in the state where the treatment tool is inserted into the endoscope.

2. The biopsy system according to claim 1, wherein a length and a position of the flattened portion are configured so that the flattened portion extends over a total length of the bending portion, in both a state where the needle tube is maximally advanced with respect to the endoscope and a state where the needle tube is maximally retracted with respect to the endoscope, when the treatment tool for endoscopes is inserted into and fixed to the endoscope.

3. The biopsy system according to claim 1,
wherein the needle tube has an opening surface at the distal end portion, and the opening surface extends from a distal point of the needle tube to a point on the needle tube that is more proximal than the distal point;
wherein the at least one surface comprises an upper surface and a lower surface; and
wherein the distal point is aligned with the upper surface of the flattened portion and the point more proximal than the distal point is aligned with the lower surface of the flattened portion.

4. The biopsy system according to claim 1, wherein the needle tube comprises:
a first connecting portion connecting the distal end portion with the flattened portion, the first connecting portion having a dimension in a direction of the minor axis which increases in a taper angle in a direction moving away from the flattened portion toward the distal end portion; and
a second connecting portion connecting the proximal end portion with the flattened portion, the second connecting portion having a dimension in a direction of the minor axis which increases in a taper angle in a direction moving away from the flattened portion toward the proximal end portion; and
wherein the taper angle of the first connecting portion is greater than the taper angle of the second connecting portion.

5. The biopsy system according to claim 1,
wherein the treatment tool has a treatment tool operation unit configured to operate the needle tube,
the fixing unit is a holder that is provided at a distal end portion of the treatment tool operation unit, the holder having a pair of wall portions, and
the operation section of the endoscope is inserted through a space between the pair of wall portions, the treatment tool operation unit is fixed to the endoscope to fix the operation section such that the minor axis becomes parallel to the bending plane.

6. The biopsy system according to claim 5,
wherein the treatment tool operation unit has an operation body, a needle slider to which the needle tube is fixed and is slidably attached to the operation body, and a stopper that has a fixing screw, the stopper being attached to the operation body in order to regulate a movement range of the needle slider, and
wherein an axis of the fixing screw is arranged toward an axis of the operation section of the endoscope in a state where the treatment tool is fixed to the endoscope.

7. The biopsy system according to claim 1, wherein the endoscope is an ultrasonic endoscope having an ultrasonic scanning mechanism provided on a distal end side of the bending portion.

8. The biopsy system according to claim 1,
wherein the cross-section of the flattened portion is oval;
wherein the cross-section of the distal end portion is circular such that the major axis of the distal end portion is equal to the minor axis of the distal end portion; and
wherein the cross-section of the proximal end portion is circular such that the major axis of the proximal end portion is equal to the minor axis of the proximal end portion.

* * * * *